United States Patent
Jung et al.

(10) Patent No.: US 8,353,900 B2
(45) Date of Patent: *Jan. 15, 2013

(54) MINIATURE CIRCULAR MAPPING CATHETER

(75) Inventors: Eugene Jung, Nesconset, NY (US); Dong Ik Shin, Poway, CA (US); Eric Scott Vaughan, Washington, DC (US); James Savage, San Diego, CA (US); Robert C. Pacheco, Bayside, NY (US); Jaime Merino, Elmont, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 893 days.

This patent is subject to a terminal disclaimer.

(21) Appl. No.: 12/218,191

(22) Filed: Jul. 11, 2008

(65) Prior Publication Data

US 2009/0043186 A1 Feb. 12, 2009

Related U.S. Application Data

(63) Continuation-in-part of application No. 11/891,065, filed on Aug. 8, 2007, now Pat. No. 7,860,578.

(51) Int. Cl.
*A61B 18/18* (2006.01)
(52) U.S. Cl. ............... 606/21; 606/27; 606/28; 606/37; 606/41; 606/45; 606/49; 606/50
(58) Field of Classification Search .................. 600/374, 600/381; 604/20, 121; 606/15, 21, 37, 41, 606/45, 49–50, 14, 27, 28
See application file for complete search history.

(56) References Cited

U.S. PATENT DOCUMENTS

| | | | | |
|---|---|---|---|---|
| 5,257,635 A | * | 11/1993 | Langberg | 607/122 |
| 5,295,484 A | | 3/1994 | Marcus et al. | |
| 5,478,330 A | * | 12/1995 | Imran et al. | 604/526 |
| 5,582,609 A | | 12/1996 | Swanson et al. | |
| 5,626,136 A | | 5/1997 | Webster, Jr. | |
| 5,680,860 A | | 10/1997 | Imran | |
| 5,755,663 A | * | 5/1998 | Larsen et al. | 600/374 |
| 5,843,152 A | * | 12/1998 | Tu et al. | 607/122 |
| 5,860,920 A | | 1/1999 | McGee et al. | |
| 5,971,983 A | | 10/1999 | Lesh | |
| 6,004,269 A | | 12/1999 | Crowley et al. | |

(Continued)

FOREIGN PATENT DOCUMENTS

EP 1457225 9/2004

(Continued)

*Primary Examiner* — Bhisma Mehta
*Assistant Examiner* — Edelmira Bosques
(74) *Attorney, Agent, or Firm* — Seager, Tufte & Wickhem, LLC

(57) ABSTRACT

An ablation device, including a catheter and an ablation element incorporating one or more balloons at the distal end of the catheter, has a continuous passageway extending through it from the proximal end of the catheter to the distal side of the expandable ablation element. The ablation device ablates tissue by subjecting it to ultrasound energy, cryogenic energy, chemical, laser beam, microwave, or radiation energy. A probe carrying electrodes is introduced through this passageway and deploys, under the influence of its own resilience, to a structure incorporating a loop which is automatically aligned with the axis of the expandable ablation device, so that minimal manipulation is required to place the probe. Pulmonary vein potential is monitored in real time via the electrodes. The probe may have an atraumatic tip with a ball formed at the leading edge. The atraumatic tip prevents any tissue damage such as perforation of heart wall.

12 Claims, 12 Drawing Sheets

U.S. PATENT DOCUMENTS

| | | |
|---|---|---|
| 6,237,605 B1 | 5/2001 | Vaska et al. |
| 6,315,778 B1 | 11/2001 | Gambale et al. |
| 6,325,797 B1 | 12/2001 | Stewart et al. |
| 6,605,084 B2 | 8/2003 | Acker et al. |
| 6,628,976 B1 | 9/2003 | Fuimaono et al. |
| 6,635,054 B2 | 10/2003 | Fjield et al. |
| 6,645,199 B1 | 11/2003 | Jenkins et al. |
| 6,702,811 B2 | 3/2004 | Stewart et al. |
| 6,771,996 B2 | 8/2004 | Bowe et al. |
| 6,808,524 B2 | 10/2004 | Lopath et al. |
| 7,860,578 B2 * | 12/2010 | Jung et al. .............. 607/122 |
| 2002/0032441 A1 * | 3/2002 | Ingle et al. .............. 606/41 |
| 2003/0060821 A1 | 3/2003 | Hall et al. |
| 2003/0069521 A1 * | 4/2003 | Reynolds et al. .............. 600/585 |
| 2003/0069578 A1 | 4/2003 | Hall et al. |
| 2004/0176757 A1 | 9/2004 | Sinelnikov et al. |
| 2004/0181137 A1 | 9/2004 | Rodriguez et al. |
| 2006/0106295 A1 | 5/2006 | Jais et al. |
| 2006/0287592 A1 | 12/2006 | Rodriguez et al. |
| 2008/0249518 A1 | 10/2008 | Warnking et al. |

FOREIGN PATENT DOCUMENTS

| | | |
|---|---|---|
| WO | WO-2005102199 | 11/2005 |
| WO | WO-2006055534 | 5/2006 |

* cited by examiner

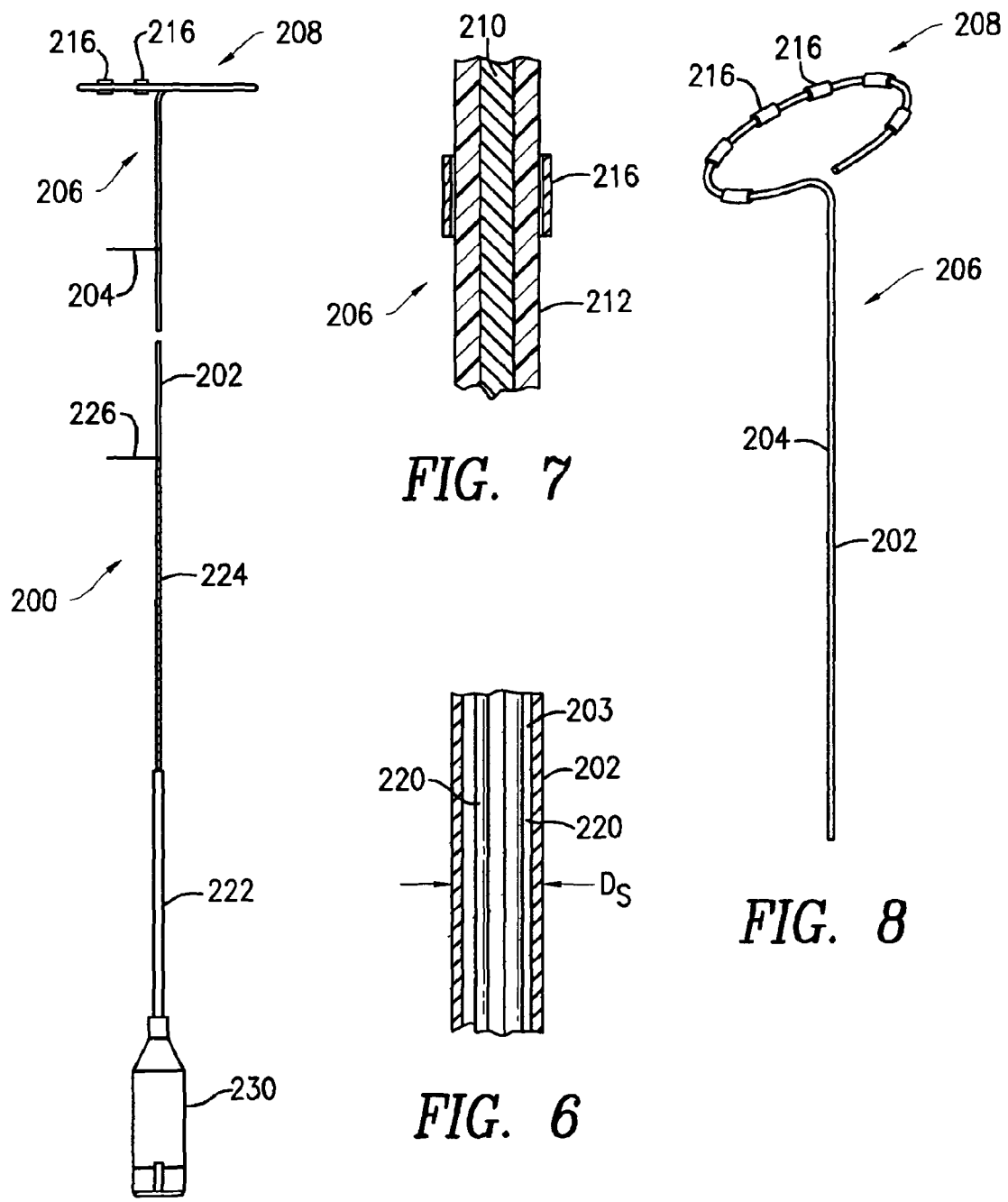

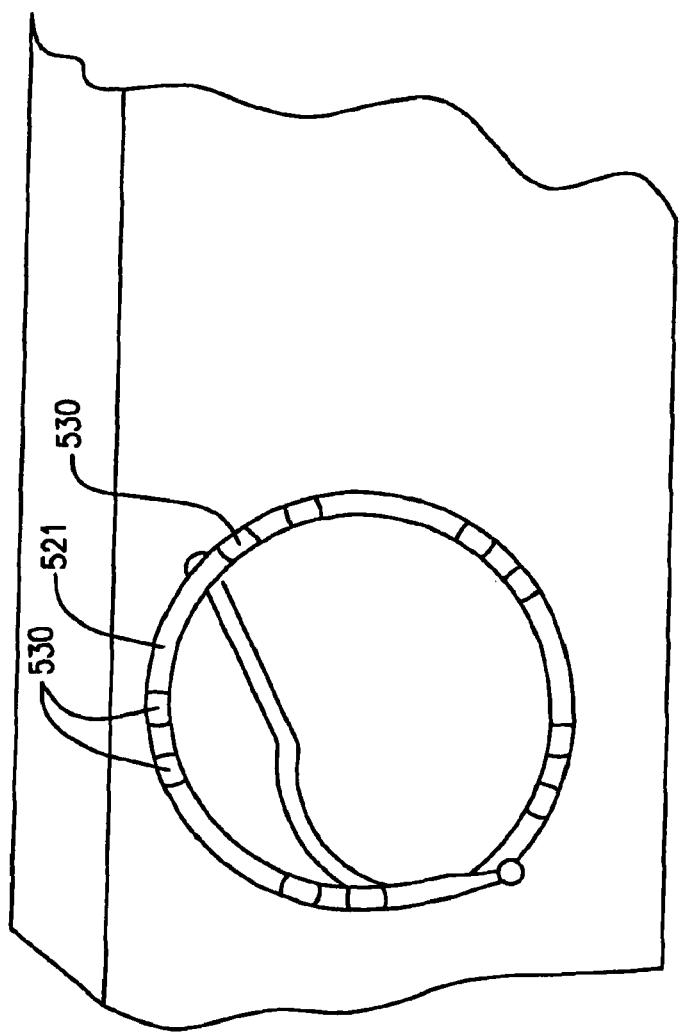
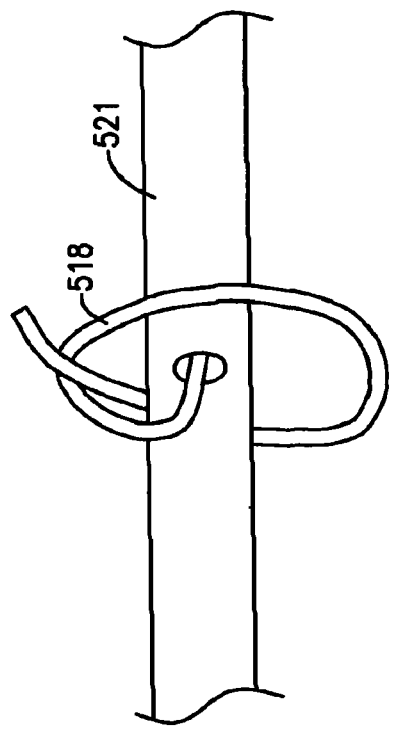

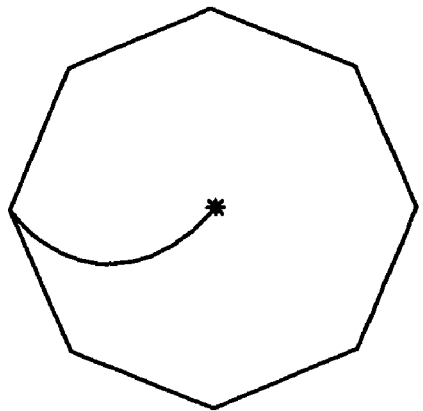
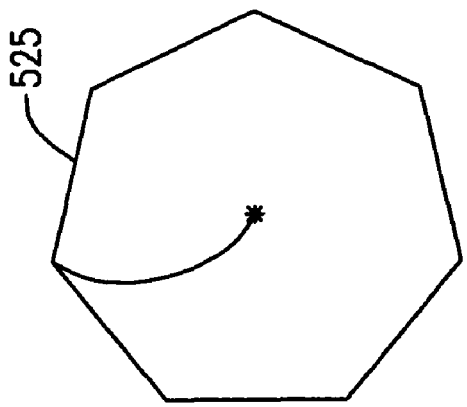
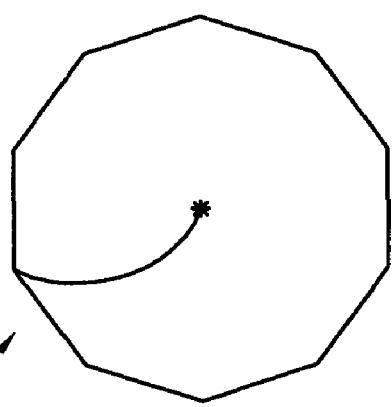
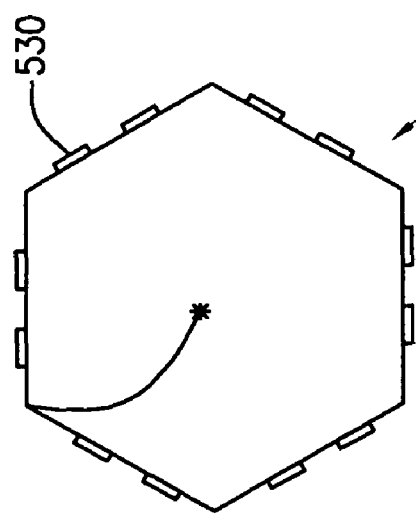
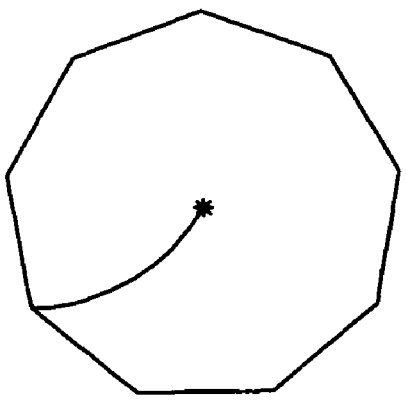
FIG. 15A

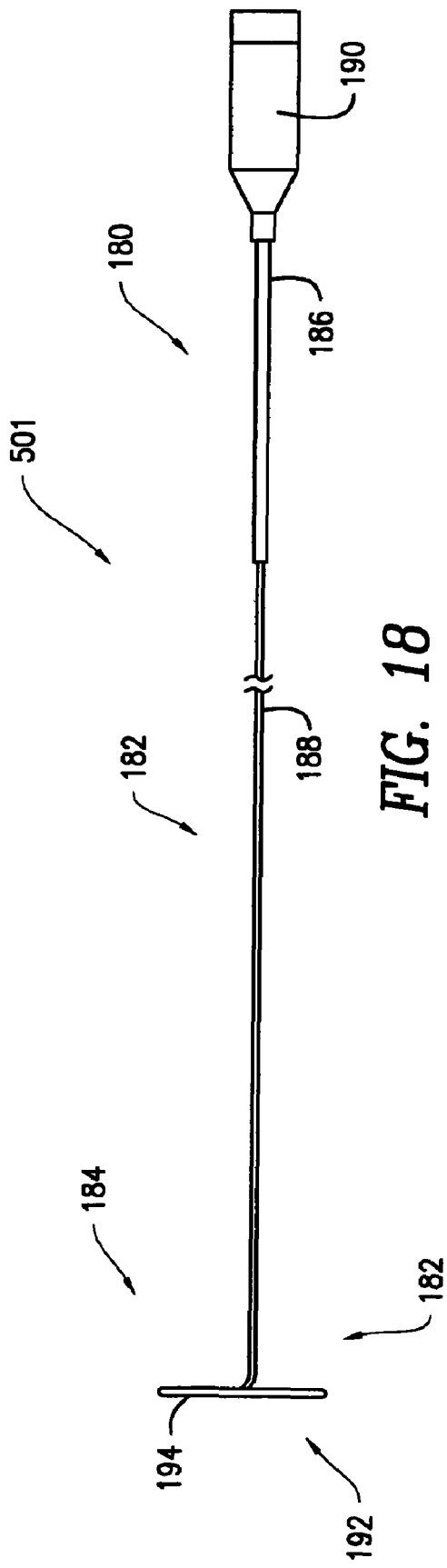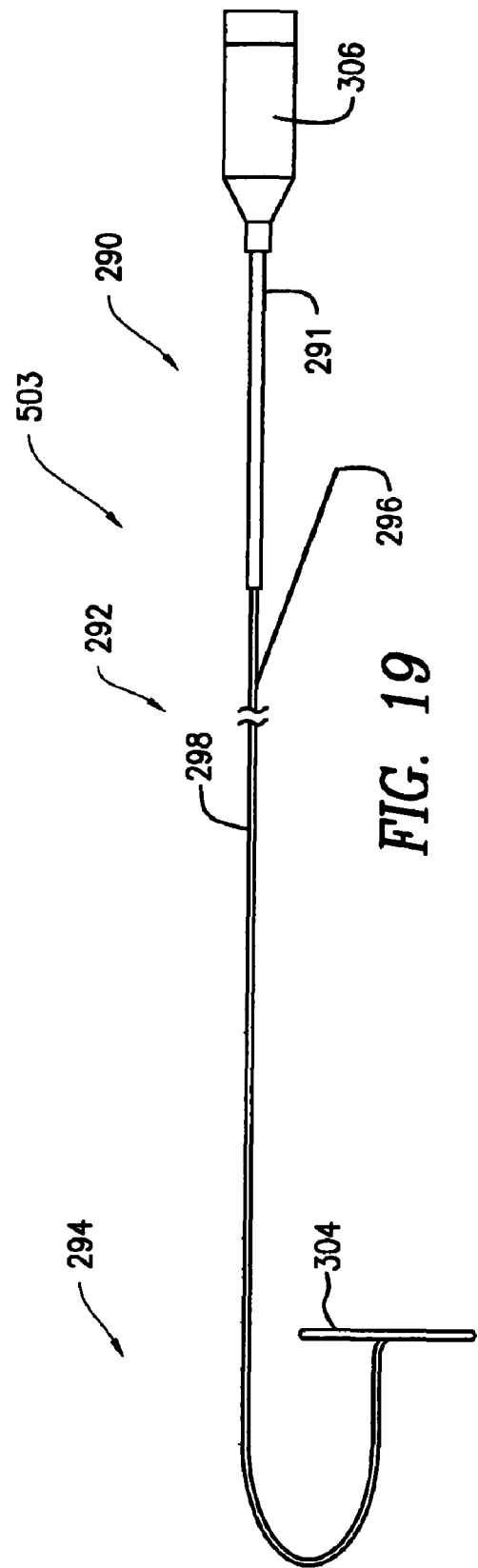

MINIATURE CIRCULAR MAPPING CATHETER

CROSS-REFERENCE TO RELATED APPLICATIONS

This application is a continuation-in-part of U.S. application Ser. No. 11/891,065, filed on Aug. 8, 2007, the disclosure of which is incorporated herein by reference.

BACKGROUND ART

The present invention relates to apparatus and methods for cardiac ablation and to miniature sensor structures useful in such apparatus and methods.

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue along a path crossing a route of abnormal conduction, either by surgically cutting the tissue or by applying energy or chemicals to the tissue, so as to form a scar. The scar blocks the abnormal conduction. For example, in treatment of AF, it has been proposed to ablate tissue in a partial or complete loop around a pulmonary vein, within the ostium or opening connecting the vein to the heart, or within the wall of the heart surrounding the ostium. It would be desirable to perform such ablation using a catheter-based device which can be advanced into the heart through the patient's circulatory system.

As described in commonly assigned U.S. Pat. No. 6,635,054, the disclosure of which is incorporated by reference herein, an expansible structure is used as a reflector for directing and focusing ultrasonic waves from an ultrasonic transducer into a region of tissue to be ablated. This arrangement can be used, for example, to treat atrial fibrillation by ablating a circular region of myocardial tissue encircling the ostium of a pulmonary vein. The ablated tissue forms a barrier to abnormal electrical impulses which can be transmitted along the pulmonary veins and, thus, isolates the myocardial tissue of the atrium from the abnormal impulses. As disclosed in commonly assigned U.S. Provisional Patent Application Ser. No. 60/448,804, filed Feb. 20, 2003, and in commonly assigned, co-pending U.S. Published Patent Application No. 2004/0176757 (hereinafter "the '757 application") and PCT International Application No. PCT/US04/05197, the disclosures of which are incorporated by reference herein, a catheter-carried expansible ablation structure as disclosed in the '054 patent can be equipped with a steering mechanism so that the orientation of the expansible structure relative to the heart can be controlled by the physician without relying upon physical engagement with the pulmonary vein or pulmonary vein ostium.

It is often desirable to monitor electrical signals propagating within the heart. For example, McGee et al., U.S. Pat. No. 5,860,920, discloses a structure incorporating an elongated element with numerous electrodes disposed along a distal region of the structure. The structure is advanced into the heart within a guide tube or sheath, which is then retracted so as to expose the distal region. In this condition, the distal region, under its own resilience, forms itself into a hoop shape, which can be pressed into engagement with a region of the heart wall as, for example, a region surrounding the bicuspid valve or the mitral valve. The electrodes pick up electrical signals propagating within the heart. The electrodes can be connected to a source of electrical energy, so that the electrical energy applied through the electrodes ablates the cardiac tissue. Swanson et al., U.S. Pat. No. 5,582,609, discloses another loop-forming structure carrying electrodes for electrical ablation. Fuimaono et al., U.S. Pat. No. 6,628,976, discloses a catheter with a similar loop-like structure said to be useful in mapping electrical activity or "wavelets" within a pulmonary vein, coronary sinus or other "tubular structure" prior to treatment of the condition.

Marcus et al., U.S. Pat. No. 5,295,484, discloses a catheter carrying both an ultrasonic transducer and electrodes for sensing electrical potentials within the heart. These electrodes can be used to allow the physician to determine whether the arrhythmia has persisted after the ablation process. Also, the aforementioned '054 patent and '054 patent disclose, in certain embodiments, expansible balloon structures having ring-like electrodes thereon for detecting electrical signals within the heart.

Despite all of these efforts in the art, however, still further improvement would be desirable. Particularly, providing sensing structures that prevent damage to the tissue and are capable of passing through a lumen smaller than one millimeter is desirable. Providing electrical sensing structures on a balloon-like or other expansible ablation device complicates fabrication of the device and makes it more difficult to make the device collapse to a small diameter for advancing or withdrawing the device through the vascular system. Further, mounting the electrodes on the same catheter as an ultrasonic transducer, as disclosed in the '484 patent, limits placement of the electrodes and the configuration of the transducer array and associated structures. The particular structures shown in the '484 patent, for example, are not well suited to formation of a ring-like lesion or sensing of electrical potentials at numerous locations. Use of a loop-forming sensing element entirely divorced from an ablation device, as contemplated in U.S. Pat. No. 6,628,976, necessarily requires separate steps for placement of such a device which adds both complexity and risk to the procedure. Thus, there is a need for a sensing probe that can be used with various ablation devices (for example, ablation devices that use cryogenic energy or laser energy or microwave energy or radiation energy or radio frequency or ultrasound energy or chemical ablation) without requiring separate steps for placement of the probe and the ablation device.

SUMMARY OF THE INVENTION

One aspect of the present invention provides apparatus for cardiac treatment which includes a catheter having proximal and distal ends and a lumen, as well as an expansible ablation device mounted at or near the distal end of the catheter. The ablation device has a collapsed condition and an expanded condition, and is operative to apply energy to cardiac tissues in proximity to the device when the device is in the expanded condition. In its expanded condition, the device and catheter define a port open to the exterior of the expansible ablation device on the distal side of the device. Desirably, the ablation device defines a bore extending through the ablation device. The bore has a first end communicating with the lumen and a second end defining the port.

Apparatus according to this aspect of the invention desirably also includes an elongated sensor probe which also has proximal and distal ends. The sensor probe includes one or more electrodes disposed adjacent the distal end of the sensor probe. The lumen and the ablation device are constructed and arranged so that the sensor probe can be removably positioned in the passageway, with the distal end of the sensor probe projecting out of the ablation device through the port. The sensor probe has a distal section and a floppy section formed in the distal section. The distal most tip of the sensor probe has a ball formed thereon. The floppy section has a wire core and a polymeric tube covering the wire core. The polymeric tube is made from a soft material such as a thermoplastic elastomer or a polyether block amide and has a low durometer value, for example, 35-72 Shore D. An example of the soft material is PEBA, polyether block amide, such as the polymers sold under the trademark PEBAX®. The wire and the polymeric tube are in engagement in the area near the ball such that there is no relative motion between them in the area near the ball.

A further aspect of the invention provides methods of cardiac ablation which include the steps of advancing an apparatus including a catheter and an expansible ablation device into the subject while the ablation device is in a collapsed condition, until the ablation device is disposed in a chamber of the subject heart, and then expanding the ablation device to an expanded condition. In a method according to this aspect of the invention, the ablation device desirably is positioned in a desired disposition relative to the heart and actuated to apply energy in a loop-like region having a predetermined spatial relationship to the ablation device, and thereby ablate the tissue in this region so as to form a lesion. Methods according to the invention desirably further include the step of advancing a sensing probe with atraumatic tip having a floppy section with a ball formed at the leading edge, through a continuous passageway from the proximal end of the catheter through the ablation device, so that a distal region of the sensing probe projects out of a port on the ablation device and contacts tissue of the subject adjacent the ablation device. In methods according to this aspect of the invention, the ablation device desirably at least partially positions the projecting distal region of the sensing probe relative to the heart. The method desirably further includes the step of detecting electrical signals in the subject using the sensing probe. Methods according to this aspect of the invention afford advantages similar to those discussed above in connection with the apparatus.

Yet another aspect of the invention provides a probe having a proximal end and a distal end. A ball is formed at the tip of the distal end. A floppy section is attached to the ball. The floppy section has a wire core and a polymeric tube covering the wire core. The polymeric tube is made from a soft material such as Pebax®. The wire core and the polymeric tube are in engagement in the area near the ball such that there is no relative motion between them in the area near the ball. In its deployed condition, the probe body desirably is hoop shaped. The hoop desirably carries one or more of the functional elements such as the electrodes.

Yet another aspect of the invention provides a probe having a proximal end and a distal end. A ball is formed at the tip of the distal end. A floppy section is attached to the ball. The floppy section has a wire core and a polymeric tube covering the wire core. The polymeric tube is made from a soft material such as PEBA. The wire core and the polymeric tube are in engagement in the area near the ball such that there is no relative motion between them in the area near the ball. In its deployed condition, the probe body desirably is hoop shaped. The hoop desirably carries one or more of the functional elements such as the electrodes.

Yet another aspect of the invention provides an apparatus for cardiac treatment. The apparatus comprises an ablation device adapted to ablate cardiac tissue using cryogenic energy. The ablation device having a catheter having an inner balloon and a safety balloon mounted on the catheter. The catheter also having a first lumen and an injection tube. A sensor probe for sensing electric potential of cardiac tissue is insertable through the first lumen and refrigerant can be injected in the inner balloon via the injection tube.

In yet another aspect the invention provides a method of ablating cardiac tissue. The method includes inserting a catheter having an ablation device in a chamber of a heart; inserting a sensor probe in a lumen in the catheter; ablating the cardiac tissue by exposing the cardiac tissue to an ablating energy; monitoring the effect of ablating energy in real time by sensing the pulmonary vein potentials via electrodes located on the sensor probe; and deciding based upon the levels of the sensed pulmonary vein potentials whether to continue ablating in same location or to reposition the ablation device.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 5 is a diagrammatic elevational view of a probe in accordance with a second embodiment of the invention.

FIG. 6 is a fragmentary diagrammatic sectional view depicting a portion of the probe shown in FIG. 5.

FIG. 7 is a fragmentary diagrammatic sectional view depicting a further portion of the probe shown in FIG. 5.

FIG. 8 is a diagrammatic perspective view depicting a portion of the probe shown in FIG. 5.

FIG. 15 is a view of the loop end of sensor probe of FIG. 13 as seen from an angle.

FIG. 15A shows another embodiment of a loop formed at the distal end of sensor probes.

FIG. 16 is a schematic view showing the electrode wire exiting from a hole in the PEBA tube in tip section.

FIG. 18 shows another embodiment of a sensor probe.

FIG. 19 shows yet another embodiment of a sensor probe that is steerable.

DETAILED DESCRIPTION

Figure 1:
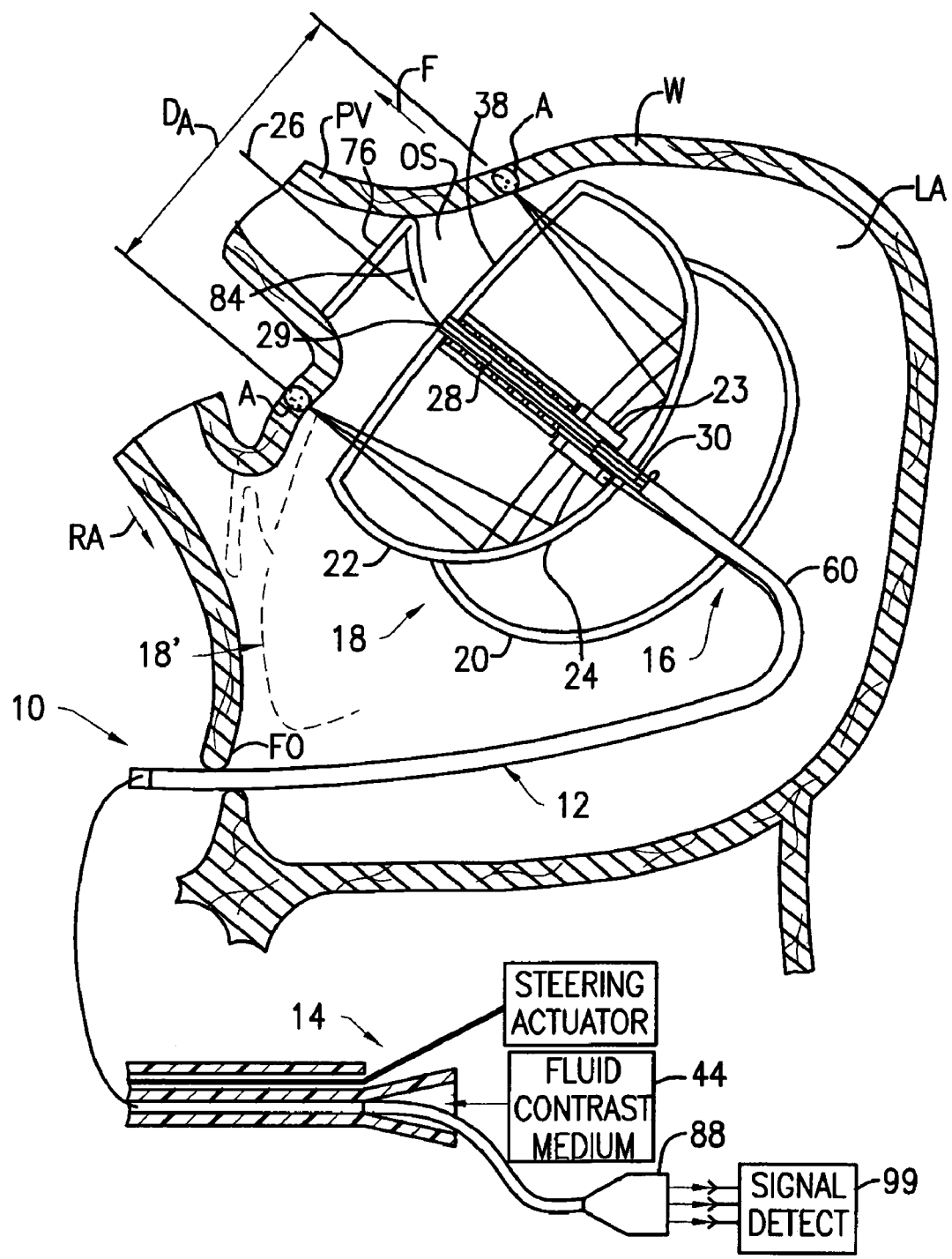
FIG. 1 is a diagrammatic, partial sectional view of apparatus in accordance with one embodiment of the invention during one stage of a method in accordance with an embodiment of the invention.

As seen in FIG. 1, apparatus according to one embodiment of the invention includes an insertable structure 10 incorporating an elongated catheter 12 having a proximal end 14, which remains outside of the body, and a distal end 16 adapted for insertion into the body of the subject. As used in this disclosure with reference to structures which are advanced into the body of a subject, the "distal" end of such a structure should be taken as the end which is inserted first into the body and which penetrates to the greatest depth within the body, whereas the proximal end is the end of the structure opposite to the distal end. Insertable structure 10 also includes an ablation unit 18 mounted to catheter 12 adjacent distal end 16. Ablation unit 18 incorporates a reflector balloon 20 and a structural balloon 22 having a common wall 24. Reflector balloon 20 is linked to an inflation lumen (not shown) in catheter 12, which extends to the proximal end of catheter 12 and which is connected, during use, to a source of a gas under pressure, such as air or, more preferably, carbon dioxide, as, for example, to a gas-filled hypodermic syringe, so that reflector balloon 20 can be inflated with a gas. Structural balloon 22 is connected through a separate inflation lumen (not shown) to a source of a liquid such as isotonic saline solution, so that structural balloon 22 can be inflated with the liquid. A cylindrical ultrasonic emitter 23 is mounted within structural balloon 22. Balloons 20 and 22, and particularly the common wall 24 separating balloons 20 and 22, are designed so that in their inflated, operative condition illustrated in FIG. 1, balloons 20 and 22 are in the form of bodies of revolution about a central or forward-to-rearward axis 26. Emitter 23 is cylindrical and is coaxial with balloons 20 and 22.

A tube defining a bore 28 extends through structural balloon 22 at central axis 26. Tube bore 28 communicates with a port 29 on or forward of a forward wall 38 of structural balloon 22. Tube bore 28 also communicates with a lumen 30 within catheter 12. Lumen 30 extends to proximal end 14 of catheter 12 and is provided with a suitable fluid connection such as a Luer hub. Tube bore 28 and lumen 30 together form a continuous passageway extending from outlet port 29, just distal to the ablation device back to proximal end 14 of catheter 12. The tube defining bore 28 may be formed from a material such as an expanded polymer of the type commonly used in vascular grafts, so that the interior bore 28 of the tube remains patent when the tube is stretched.

The common wall 24 separating balloons 20 and 22 forms an active, reflective interface. This active interface desirably has the form of a surface of revolution of a parabolic section around central axis 26. When balloons 20 and 22 are in their inflated, expanded configuration shown in FIG. 1, ultrasonic waves emitted by emitter 23 are directed radially outwardly away from axis 26 and impinge on the parabolic active interface formed by common wall 24, where it is reflected forwardly and slightly outwardly away from axis 26 and focused so that the ultrasonic waves emitted along various paths mutually reinforce within a ring-like ablation region A, just forward of forward wall 38 of structural balloon 22 encircling axis 26. The focused ultrasonic waves in this region can effectively ablate myocardial tissue and form a substantial conduction block extending through the heart wall in a relatively short time, typically about a minute or less. The ablation unit 18 can be selectively steered to position it in a desired orientation for ablating the tissue in a desired location.

Figure 2:
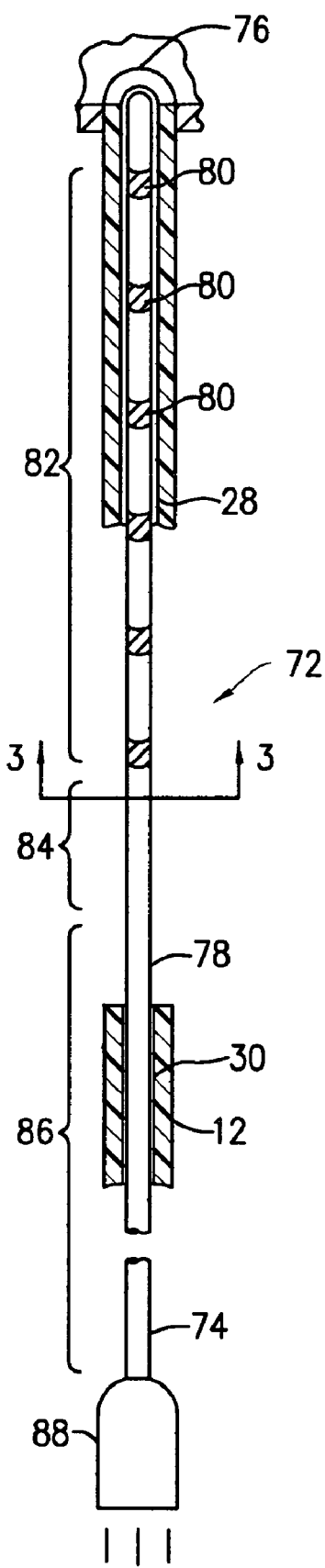
FIG. 2 is a fragmentary, diagrammatic perspective view depicting components of the apparatus shown in FIG. 1 at another stage in the method.
Figure 3:
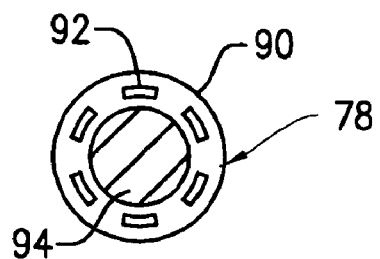
FIG. 3 is a diagrammatic sectional view taken along line 3-3 in FIG. 2.

The apparatus further includes an elongated sensor probe 72 (FIG. 2) having a proximal end 74 and a distal end 76. Probe 72 includes an elongated resilient body having a diameter smaller than the inside diameter of lumen 30. A plurality of electrodes 80 (FIGS. 2 and 4) extend around resilient probe body 78 in an operative region 82 adjacent distal end 76 of probe 72, also referred to as a "hoop region." The probe body 78 also includes a juncture region 84 disposed proximal to operative region 82 and a main or base region 86 extending from juncture region 84 to proximal end 74 of probe 72. A connector 88 is provided at proximal end 74 of probe 72. As best seen in FIG. 3, resilient body 78 includes a dielectric layer 90 and conductors 92 extending within dielectric layer 90 from electrodes 80 to connector 88 (FIG. 2). Probe body 78 also includes a resilient metallic element 94 extending along the length of probe body 78. Element 94 may be a super elastic material such as an alloy of nickel and titanium, commonly referred as nitinol. The particular arrangement depicted in FIG. 3, with conductors 92 disposed around resilient element 94, is not essential. For example, conductors 92 may be grouped to one side of elastic element 94. Probe 72 can be placed into the continuous passageway defined by the catheter lumen 30 and bore 28, and can be removed therefrom.

Figure 4:
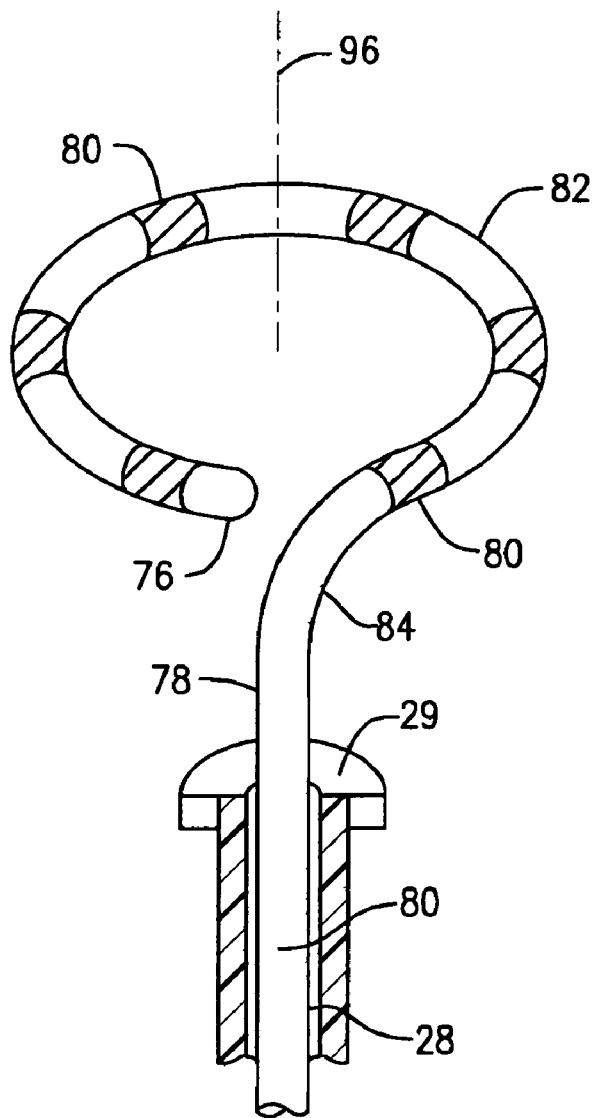
FIG. 4 is a diagrammatic perspective view of the components illustrated in FIG. 2 during another stage in the method.

In its free or unconstrained condition, resilient body 78 assumes the shape depicted in FIG. 4. In this shape, hoop region forms a generally circular hoop 82 (alternatively referred to as "loop") in a plane transverse to an axis 96 defined by the distal-most part of base region 86. Hoop 82 encircles axis 96 and is substantially coaxial therewith. The connecting or transition region 84 extends outwardly from axis 96 and also slopes slightly in the forward or distal direction. As discussed below, the probe body is in this unconstrained state when deployed within the heart, and accordingly, this condition is also referred to herein as the "deployed" condition of the probe body. The distal portion of the hoop region may be of an atraumatic design similar to one shown in FIG. 10 and described in detail hereafter. In a variation of the embodiment shown in FIG. 4, the hoop region and juncture region 84 may have the shape described in detail hereafter and depicted in FIGS. 11 and 12.

A sensor probe in accordance with a second embodiment of the invention has a composite body 200 (FIG. 5) including a tubular metallic shaft section 202 which may be formed from a stainless steel tube of the type commonly used to form hypodermic needles. Shaft section 202 defines an interior bore 203 (FIG. 6). Desirably, shaft section 202 has an outside diameter $D_s$ (FIG. 6) on the order of 1.25 mm or less, more desirably about 1 mm (0.040 inches) or less, and most preferably about 0.9 mm (0.035 inches). Preferably, shaft section 202 extends throughout the majority of the length of probe 200. For example, shaft section 202 may be on the order of 140 cm (55 inches) long.

A distal section 206 is mounted to the distal end 204 of shaft section 202. Distal section 206 includes a wire core 210 (FIG. 7) with a dielectric, biologically inert polymeric covering 212 overlying the core. The core desirably is formed from a metal such as a nickel-titanium alloy which can be formed to a preselected shape and which will tend to return to the preselected shape when unconstrained. A plurality of electrodes 216 overlie covering 212 in a portion of the length of distal section 206. As best seen in FIG. 8, this portion 208 of distal section 206 in its free or unconstrained condition forms a hoop lying in a plane transverse to the axis defined by the remainder of distal section 206. In the free or unconstrained condition, distal 206 section may extend about 5 cm (2 inches) proximally from the plane of the hoop. Distal section 206 is formed to this hoop shape and tends to return to this shape when distal section 206 is unconstrained. However, distal section 206 is quite flexible, and hence, can be constrained to a straight or gently curving shape, so as to be advanced through the passageway defined by the catheters and ablation devices discussed above. Shaft section 202 is flexible enough to pass through gently curving portions of the catheter but is considerably stiffer than distal section 206.

Figure 10:
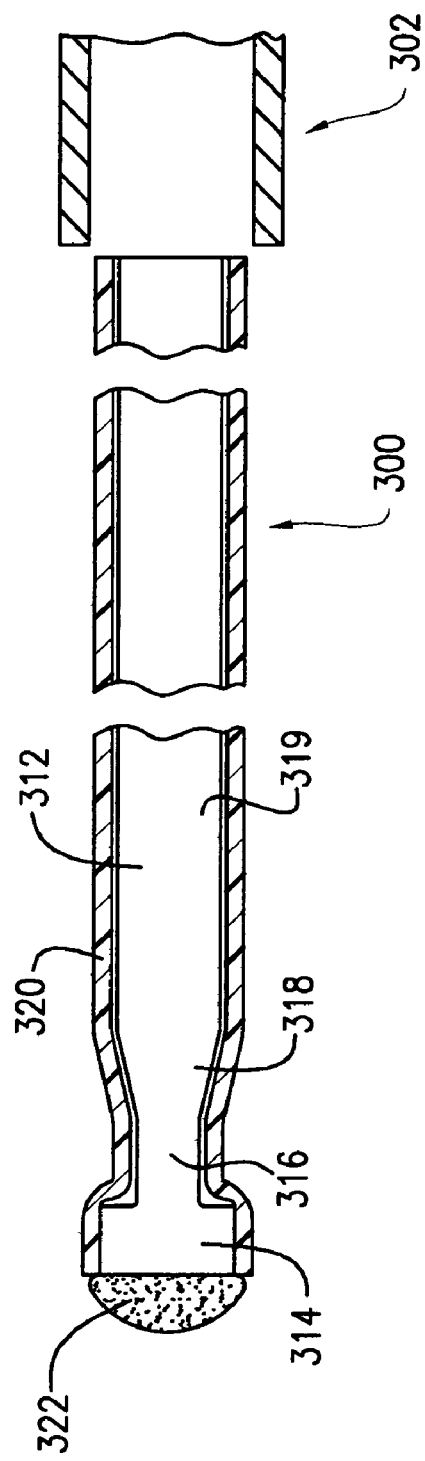
FIG. 10 is a schematic view of the atraumatic tip of the third embodiment.

The proximal end of distal section 206 abuts distal end 204 of shaft section 202 and is bonded to shaft section 202. Desirably, wire core 210 extends into bore 203 of shaft section 202 a short distance from this abut joint. A plurality of fine insulated wires 220 are disposed within bore 203 of shaft section 202. These wires 220 are electrically connected to electrodes 216 on distal section 206. The probe body also includes a proximal section 222 and a transition section 224 extending from proximal section 222 to proximal end 226 of shaft section 202. The proximal end section may include a relatively stiff polymeric tube having an interior bore (not shown). Transition section 224 may include a polymeric tube having stiffness intermediate between that of the proximal end section and shaft section 202, this tube also having an interior bore. The interior bores of the transition section 224 and proximal section 222 may communicate with the bore of shaft section 202. Alternatively, the metallic tube forming shaft section 202 may extend through the interior bores of transition section 224 and proximal section 222. In either arrangement, wires 220 may extend all the way to the proximal end of proximal end section 222. An electrical connector 230 is connected to these wires and, hence, to electrodes 216. An atraumatic tip may be formed at the end region of distal section 206. The details of construction of the atraumatic tip are shown in FIG. 10 and discussed in detail hearafter. In a variation of the second embodiment, distal section 206 may have the shape described in detail hereafter and depicted in FIGS. 11 and 12.

Figure 9:
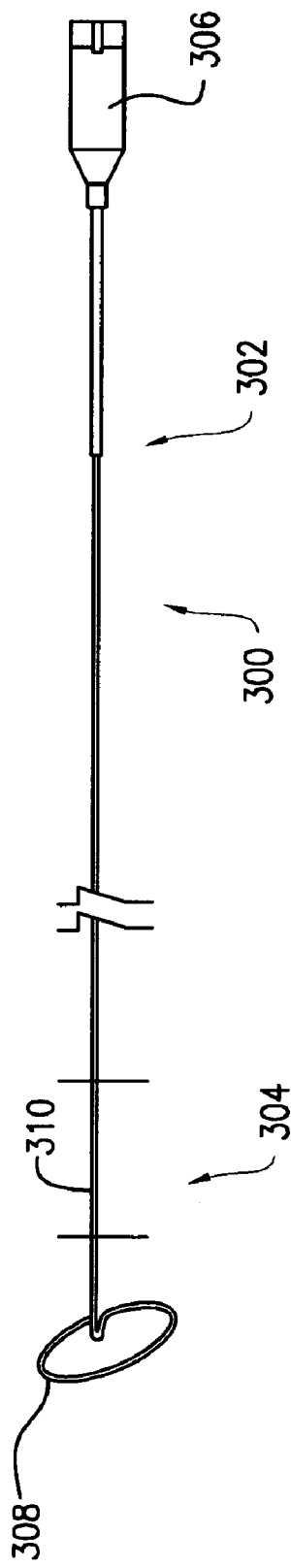
FIG. 9 is a diagrammatic elevational view of a probe in accordance with a third embodiment of the invention.
Figure 11:
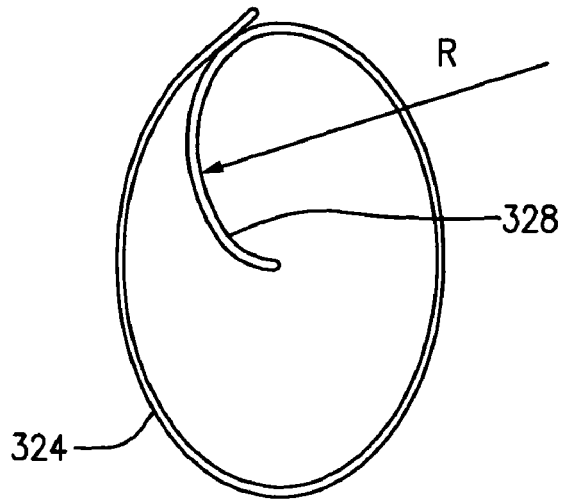
FIG. 11 shows an elevational view of the hoop region of the third embodiment.
Figure 12:
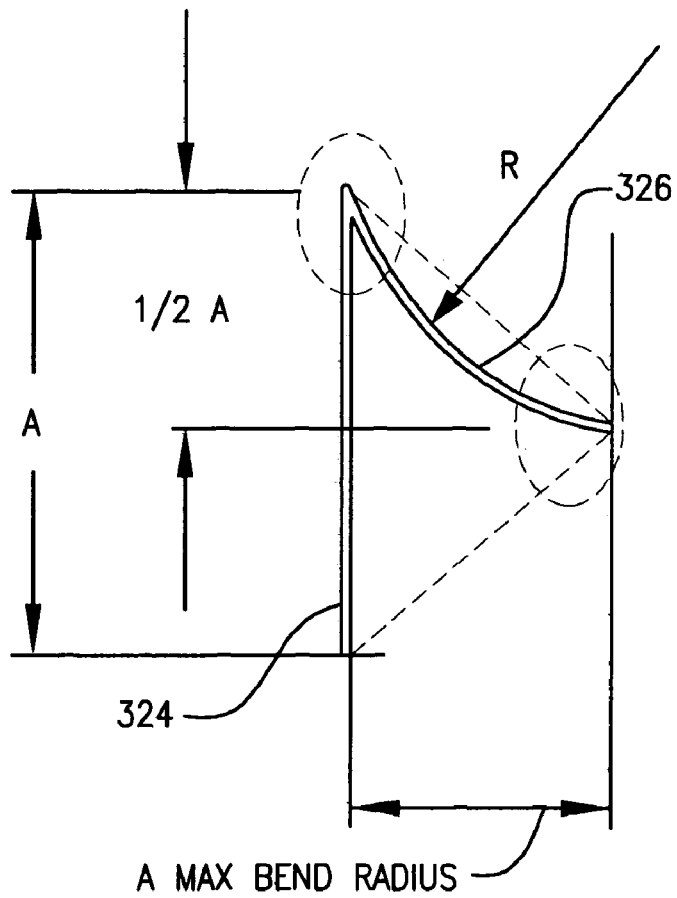
FIG. 12 shows a side view of the hoop region of the third embodiment.

A sensor probe 300 in accordance with a third embodiment of the invention is shown in FIG. 9. Sensor probe 300 has a proximal section 302 and a distal section 304. Proximal section 302 is approximately 90 percent of the length of sensor probe 300. Proximal section 302 includes a stainless steel hypotube coated with Teflon. The stainless steel hypotube provides pushability to the sensor probe 300 and transfers maximum force from a handle 306 to the opposite end of sensor probe 300. A core wire (not shown) runs through the proximal twelve inches of the hypotube to prevent it from collapsing during procedural manipulation. A plurality of electrodes (not shown) extend around a portion of a nitinol wire 312 (FIG. 10) that forms a loop 324 (FIG. 11). The electrodes are electrically insulated from nitinol wire 312. One example of a manner in which the electrodes may be insulated from nitinol wire 312 may be seen in FIG. 3 where the nitinol wire is designated by numeral 94. As seen in FIG. 3 insulated wires 92 are routed along probe body 78 through the dielectric layer 90 and exit dielectric layer 90 through small holes (not shown) cut into dielectric layer 90. The insulation is removed from the portion of the insulated wire 92 extending out from dielectric layer 90. The exposed wire is wrapped around probe body 78 and knotted, providing for a secure connection to probe body 78. A slightly oversized electrode made from Platinum or Pt10Ir is positioned directly over the wrapped wire then is mechanically swaged into position so that it becomes immovable and provides a seal to prevent blood leakage into probe body 78. The electrodes are wired to an electrical connector (not shown) that may be located in handle 306.

Distal section 304 consists of a loop section 308 and an intermediate section 310. Intermediate section 310 includes a polyimide shaft that is approximately 10.5 centimeters long. The polyimide shaft is resistant to compression and at the same time flexible. The polyimide shaft when pushed through a narrow pathway does not increase frictional resistance. The polyimide shaft is connected to the distal end of the hypotube and the proximal end of loop section 308. The soft PEBA tubing 320 (FIG. 10) and Polyimide tubing are bonded using a lap joint design. The distal end of the Polyimide tubing may be hot necked to accept PEBA tubing 320. PEBA tubing 320 is also necked to thin out the wall. The necked length of PEBA tube 320 is cut to 5 mm. The necked length of the Polyimide tubing is cut to 7 mm. The dies used to neck each tube are configured to enable the necked PEBA tube 320 to slip fit over the necked section of the Polyimide. PEBA tubing 320 is slipped over the necked part of the Polyimide and this is heat bonded. This heat bonding process is accomplished in two steps using a progressively tighter Teflon sleeve to ensure a strong bond and to reduce the profile of the bond to match the tubing. The proximal portion of the Polyimide is bonded to the hypotube by first inserting it over a tubing to give it an appropriate shape and thereafter inserting the shaped polyimide tubing over the wire bundle. The part over the wire bundle is inserted into the actual hypotube and heated again to mold the joint. Then, this joint is adhesive bonded by applying cyanoacrylate adhesive (marketed by Loctite corporation) between the hypotube and the molded polyimide to form a lap joint. The PEBA tube 320 is of a very soft durometer. For example, PEBA tube may have durometer range of 35-72 shore D. More preferably, the PEBA tube may have 70 shore D durometer value that allows for maximum flexibility and shapes nicely over the narrow loop radii to create a soft atraumatic tip as discussed hereafter. A single piece of PEBA tubing may be used to make the distal soft segment spanning from the proximal end bonded to the Polyimide shaft and ending at the distal end where it is fused to the ball section 314 of the nitinol wire 312.

FIG. 10 highlights the details of the atraumatic tip of loop section 308 of sensor probe 300. The core section has a wire core, which, in the FIG. 10 embodiment, is nitinol wire 312 having a diameter of approximately 0.012 inch. The distal end portion of nitinol wire 312 has four sections—a ball section 314, a reduced section 316, a tapered section 318 and a main section 319. Ball section 314 is the distal most section and is approximately 0.04 inch long. In this section the diameter of the nitinol wire is approximately 0.012 inch. Reduced section 316 is located between ball section 314 and tapered section 318. Reduced section 316 is approximately 0.12 inch in length and approximately 0.005 inch diameter. One end of tapered section 318 is connected to reduced section 316 and has a diameter equal to the reduced section 316 where they are connected. The opposing end of tapered section 318 has larger diameter equal to the diameter of main section 319 and is connected with main section 319. The diameter of the main section is 0.012 inches. A PEBA tubing 320 covers nitinol wire 312 in distal section 308. Approximately six millimeters of PEBA tubing 320 covering the distal end portion of nitinol wire 312 is heated in place around nitinol wire 312 in range of 150-250° F. for 15-30 seconds resulting in heat setting in this section. The tubing near the ball section 314 is bonded/melted at 450 deg F. for about 10-15 seconds. This results in PEBA tubing shrinking in onto the nitinol wire 312 and taking the shape of the underlying nitinol wire 312. The PEBA tubing physically locks to nitinol wire 312 at reduced section 316, ball section 314 and tapered section 318. Moreover, the PEBA tubing shrinks into tight frictional engagement with main section 319. The fusing of nitinol wire 312 and PEBA tubing locks nitinol wire 312 in place relative to the PEBA tubing and results in a unitized construction. Such construction creates a relatively stable structure that precludes independent movement of outer layers with respect to inner nitinol wire 312 and thereby allows the sensor probe to easily pass through a tight bore. A ball 322 is formed at the very distal tip of ball section 314. Ball 322 is formed from a UV cured adhesive such as Dymax 206-CTH-T, Dymax 203A-CTH-T, or Loctite 3311. Loop section 308 may be formed to loop shape by heat setting in one of the last steps of the assembly procedure. The ball 322 along with the taper formed PEBA tubing 320 and tapered nitinol wire 312 provide a highly atraumatic tip. An atraumatic tip described above may also be provided for the sensor probes shown in FIGS. 2 and 5 and described in detail previously.

Loop section 308 has loop 324 (FIG. 11). Loop 324 is formed by nitinol wire 312 arcuately bending the wire 312 in two planes perpendicular to each other. Loop 324 lies in a plane perpendicular to the longitudinal axis of nitinol wire 312. To form loop 324, the distal portion of nitinol wire 312 starts to turn away from the longitudinal axis in an arcuate manner. The radius of an arc 326 formed by nitinol wire 312 and as projected in a plane is equal to the diameter of loop 324. The plane on which arc 326 is projected passes through the center of loop 324, runs along the longitudinal axis and is angularly located with respect to loop 324 such that the measured radius is maximum it can be. Upon reaching the plane in which loop 324 is to lay, nitinol wire 312 bends to form loop 324. The diameter of loop 324 may vary between 15 and 25 millimeters. Smaller or larger loop diameter may also be employed. Nitinol wire 312, in forming loop 312, also bends arcuately as projected in the plane of loop 324. The radius of arc 328 may be approximately between 5 and 7 millimeters. The radius of arc 328 is one fourth of the diameter of loop 324. The straight part of the tip is approximately 0.197 inch long and forms the atraumatic tip. The point where the maximum loop diameter is first achieved and the point where the loop ends (i.e., where the atraumatic tip is attached to the loop) form a 30 degree angle with respect to the centre of the loop as seen in end view of loop 324. The end of arc 328 that is at the center of loop 324 is projecting radially out from the center of loop 324. The end of arc 328 that is at the circumference of loop 324 is tangential to loop 324. The tip of nitinol wire 312 turns slightly more than 360 degrees thereby forming a slight overlap in loop 324. The overlap is approximately 0.197 inches. The radius of arcs 326 and 328 are such that the loop structure is compact, sufficiently stiff to hold circular shape during use, but nonetheless capable of being straightened such that the sensor probe can pass through a lumen as small as 0.038 inches or smaller.

Figure 14:
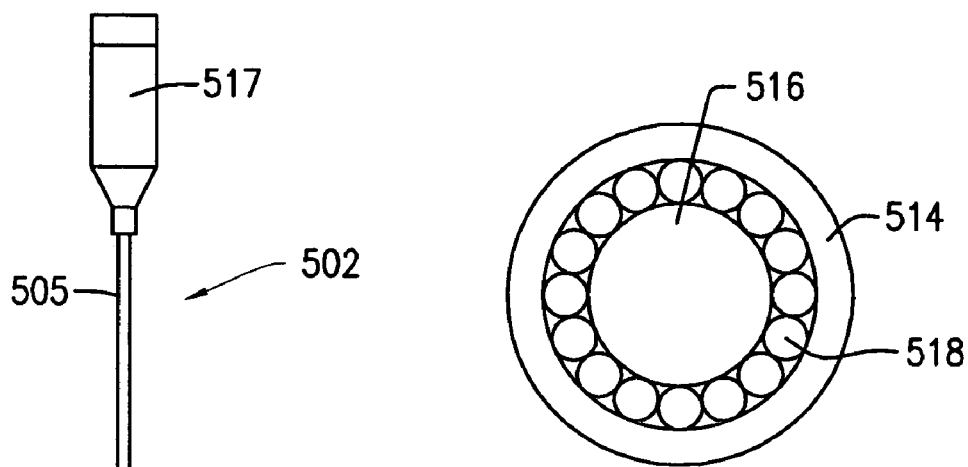
FIG. 14 is a cross-sectional view of the middle section of the sensor probe of FIG. 13.
Figure 13:
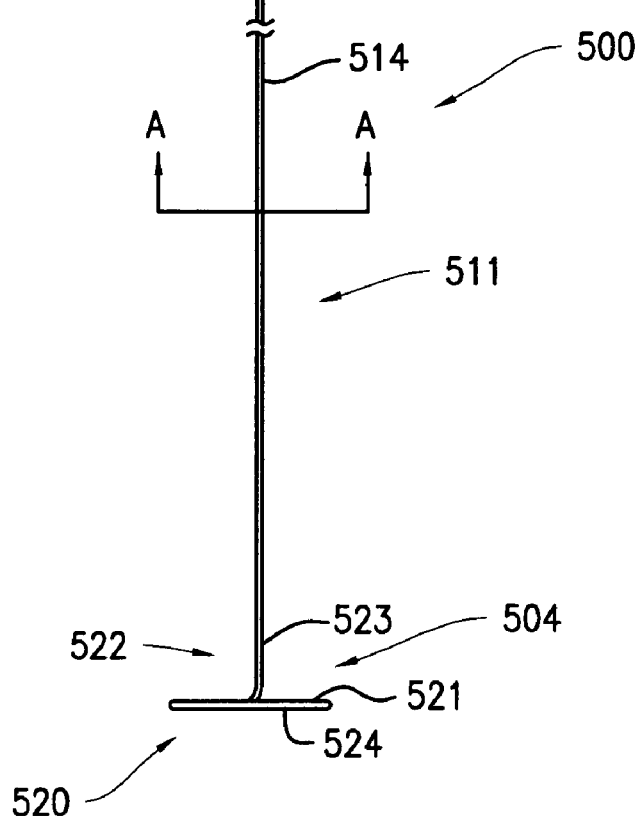
FIG. 13 is a side view of another embodiment of a sensor probe.

A sensor probe 500 in accordance with another embodiment of the invention is shown in FIG. 13. Sensor probe 500 has a proximal section 502, a distal section 504 and a middle section 511. Proximal section 502 includes a wire tube 505 made from PEBA. Middle section 511 includes a Teflon coated Nitinol shaft 514 (FIG. 14) and a Nitinol core wire 516 that is secured at its proximal end using adhesives. An electrical connector 517 is attached at the proximal end of the wire tube 505. Electrode wires 518 run from connector 517 and along the length of middle section 511 between Nitinol core wire 516 and Nitinol shaft 514. Nitinol shaft 514 provides a kink resistant shaft that efficiently transfers axial force and torque. Nitinol core wire 516 reduces ovaling when Nitinol shaft 514 is bent. Proximal end of Nitinol shaft 514 is heat bonded to the distal end of wire tube 505. The distal end of Nitinol shaft is heat bonded to the proximal end of the distal section 504.

Distal section 504 includes a distal tip section 520, a distal shaft section 522 and a loop 524. Tip section 520 has tubing 521 that may be made from PEBA. Distal shaft section 522 also has tubing 523 that may be made from polyimide. The distal end of the polyimide tubing 523 may be heat bonded to the proximal end of the PEBA tubing 521. A Nitinol core wire 526 (not shown) forms the core of the distal section 504.

A plurality of electrodes 530 (FIG. 15) are located on loop 524. Loop 524 may be concentric with the distal shaft section 522. Electrodes 530 are electrically insulated from nitinol core wire 526 by virtue of being located on the PEBA tubing 521. Insulated electrode wires 518 are routed along probe body and exit PEBA tubing 521 through small holes (FIG. 16) cut into PEBA tubing 521. The insulation is removed from the portion of the insulated electrode wire 518 extending out from PEBA tubing 521. The exposed electrode wire 518 is wrapped around probe body and knotted, providing for a secure connection to probe body. A slightly oversized electrode 530 made from Platinum or Pt10Ir is positioned directly over the wrapped wire and mechanically swaged into position so that it becomes immovable and provides a seal to prevent blood leakage into probe body. Electrodes 530 are wired to the electrical connector 517.

Electrodes 530 are located on loop 524 as pairs. Each pair has two electrodes 530 placed approximately 1.5 mm apart. Greater or smaller spacing between electrodes in a pair is also contemplated. Loop 524 may have any number of pairs of electrodes 530. For example, loop 524 may have five pairs of electrodes 530. The distance between adjacent pairs is greater than the distance between the two electrodes that form the pair. For example, the distance between adjacent pairs may be between 5-10 mm. Placing the electrodes in a pair close together (for example, 1.5 mm apart) provides a desirable electrical signal reading that is more localized to the region being measured. If the electrodes in a pair are placed further apart they pick up greater signal interference which is not desirable. Thus, it is advantageous to place electrodes 530 on loop 524 in closely spaced pairs. FIG. 15A shows examples of alternative shapes for loop 524. Loop 524 may be of a polygonal shape. The polygonal shape may be created by connecting straight segments 525. Electrodes 530 may be located on straight segments 525. Polygonal loop 524 is less susceptible to electrodes 530 mechanically interlocking with any surface as it travels through a lumen.

Distal shaft section 522 includes a polyimide tubing 523 that is resistant to compression and at the same time flexible. Polyimide tubing 523 when pushed through a narrow pathway does not increase frictional resistance. Polyimide tubing 523 is connected to the distal end of the Teflon coated Nitinol shaft 514 and the proximal end of PEBA tubing 521. Soft PEBA tubing 521 and Polyimide tubing 523 are bonded using a lap joint design. The distal end of the Polyimide tubing 523 may be hot necked to accept PEBA tubing 521. PEBA tubing 521 is also necked to thin out the wall. The necked length of PEBA tube 521 is cut to 5 mm. The necked length of the Polyimide tubing 523 is cut to 7 mm. The dies used to neck each tube are configured to enable the necked PEBA tube 521 to slip fit over the necked section of the Polyimide tubing 523. PEBA tubing 21 is slipped over the necked part of Polyimide tubing 523 and the joint is heat bonded. The heat bonding process is accomplished in two steps using a progressively tighter Teflon sleeve to ensure a strong bond and to reduce the profile of the bond to match the tubing. The proximal portion of Polyimide tubing 523 is bonded to Teflon coated Nitinol shaft 514 by first inserting it over a tubing to give it an appropriate shape and thereafter inserting the shaped polyimide tubing 523 over the electrode wire bundle. The part over the wire bundle is inserted into the Nitinol shaft 514 and heated again to mold the joint. Then, this joint is adhesive bonded by applying cyanoacrylate adhesive (marketed by Loctite corporation) between the Nitinol shaft 514 and the molded polyimide to form a lap joint. PEBA tube 521 is of a very soft durometer. For example, PEBA tube may have durometer range of 35-72 shore D. More preferably, the PEBA tube may have 70 shore D durometer value that allows for maximum flexibility and shapes nicely over the narrow loop radii to create a soft atraumatic tip as discussed previously. A single piece of PEBA tubing may be used to make the distal soft segment spanning from the proximal end bonded to the Nitinol shaft 514 and ending at the distal end where it is fused to the ball section of the nitinol wire 526. Thus, an atraumatic tip similar to one described previously is formed on sensor probe 500

In another embodiment the distal tip section 504 includes PEBA tube 521 and an anchor tube that is under PEBA tube 521. The anchor tube and PEBA tube 521 are heat bonded at their distal ends. Next, Nitinol core wire 526 is inserted in the anchor tube and the anchor tube is thermally bonded to Nitinol core wire 526. Nitinol core wire 526 is made of super elastic Nitinol and is, in part, shaped with like loop 524. The Nitinol core wire 526 forces the distal tip section to form loop 524. The distal tip section 504 may be attached to Teflon coated Nitinol shaft 514 using melt tubing made of Nylon PA 12. Nitinol shaft 514 may be a hypodermic tube that is coated with Teflon and having an uncoated section on the proximal end. Wire tube 505 may be thermally bonded to the uncoated section of Nitinol shaft 514. Nitinol shaft 514 and wire tube 505 may be coated with silicon, hydrophilic, FEP or other lubricants to add lubricity. The sensor probes may have silicone added to the distal end to give lubricity to the distal end.

Middle section 511 and distal section 504 have a diameter that is suitable for use with a lumen larger than 0.035 inch. In one embodiment the diameter of middle section 511 and distal section 504 is 0.035 inch maximum. Probes having diameters smaller or larger than 0.035 inch are also contemplated. The ball tip may be in the range of 0.030-0.035 inch. The probe diameter of about 0.035 inch is dictated by the lumen in which the probe is inserted. Thus, the diameter of about 0.035 inch can be made smaller or larger as long as the probe can be inserted in the intended lumen.

FIG. 18 shows another embodiment of sensor probe 500. The embodiment of FIG. 18 is substantially similar to the embodiment of FIG. 13, and therefore, to avoid repetition only certain features of the embodiment of FIG. 18 are described hereafter. Sensor probe 501 of FIG. 18 has a proximal section 180, a distal section 184 and a middle section 182. Proximal section 180 includes a proximal tube 186 made from PEBA. Middle section 182 includes a coated Polymeric shaft 188 and a Nitinol core wire (not shown) that is secured at its proximal end using adhesive. An electrical connector 190 is attached at the proximal end of the proximal tube 186. Electrode wires (not shown) are routed inside the proximal tube 186 from connector 190 and along the length of middle section 182 between Nitinol core wire and Polymeric shaft 188. The Nitinol core wire provides a kink resistant structure that efficiently transfers axial force and torque. Nitinol core wire reduces unwanted shaft ovaling and/or deformation when Nitinol shaft is bent. Proximal end of the Polymeric shaft 188 is heat bonded to the distal end of proximal tube 186. The distal end of Polymeric shaft 188 is heat bonded to the proximal end of the distal section 182.

Distal section includes a distal tip section 192, and a loop 194. Tip section 192 has tubing that may be made from PEBA. The distal end of the Polymeric shaft 188 may be heat bonded to the proximal end of the PEBA tubing. A Nitinol core wire (not shown) forms the core of the distal section 182. In other aspects, the construction of sensor probe 501 may be similar to that of sensor probe 500.

Figure 20:
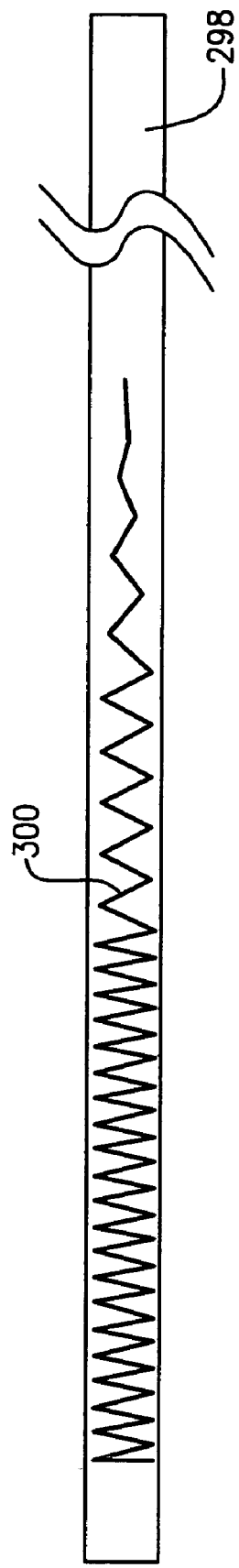
FIG. 20 shows the section of the sensor probe of FIG. 19 that is bendable.

FIG. 19 shows another embodiment of sensor probe 500. The embodiment of FIG. 19 is substantially similar to the embodiment of FIG. 13, and therefore, to avoid repetition only certain features of the embodiment of FIG. 18 are described hereafter. Sensor probe 503 of FIG. 19 has a proximal section 290, a distal section 294 and a middle section 292. Proximal section 290 includes a wire tube 291 made from PEBA and a handle (not shown) used to pull a steering tendon 296 to deflect distal end of sensor probe 503. Middle section 292 includes a Teflon coated Nitinol shaft 298. A cut 300 is formed on a distal end portion of Nitinol shaft 298 as shown in FIG. 20. Cut 300 may be on one side of the shaft i.e., cut 300 may not be all around the outer circumference of Nitinol shaft 298. Cut 300 may be about 8 mils deep. Cut 300 may be in the form of zig-zag that is spaced closer towards the distal end of Nitinol shaft 298 and have greater spread as cut 300 travels in proximal direction. Cut 200 allows the Nitinol shaft 298 to deflect in a single plane. Cut 200 is covered with a thin PEBA sleeve (not shown). The steering tendon 296 runs from the proximal handle to the distal section 294 of the sensor probe 503. The distal end of the steering tendon 296 is attached just proximal to the start of the loop 304. An electrical connector 306 is attached at the proximal end of wire tube 291. Electrode wires (not shown) run from connector 306 and along the length of middle section 292 between steering tendon 296 and Nitinol shaft 298. Nitinol shaft 298 provides a kink resistant shaft that efficiently transfers axial force and torque. The steering tendon 296 reduces ovaling when Nitinol shaft 298 is bent. Proximal end of Nitinol shaft 298 is heat bonded to the distal end of wire tube 291. The distal end of Nitinol shaft 298 is heat bonded to the proximal end of the distal section 294. In other aspects, the construction of sensor probe 503 may be similar to that of sensor probe 500.

In a method according to one aspect of the present invention, ablation device 18 is positioned within a chamber of the heart as, for example, within the left atrium LA of a subject to be treated. A guide sheath (not shown) is advanced through the venous system into the right atrium and through the septum separating the right atrium and left atrium, so that the guide sheath provides access to the left atrium. Typically, the apparatus is advanced through the guide sheath with balloons 20 and 22 in a deflated, collapsed condition. This operation may be performed by first advancing a guide wire (not shown) into the heart, and then advancing insertable structure 10, with balloons 20 and 22 in a deflated condition, over the guide wire, and through the guide sheath. During this operation, probe 72 is not present in tube bore 28 and lumen 30. The guide wire passes through tube bore 28 and through lumen 30. A guide sheath also may be used during the insertion process.

When ablation device 18 is disposed inside the heart chamber, the physician manipulates device 18 to vary the orientation of ablation device 18, and hence the orientation of forward-to-rearward axis 26, until device 18 is positioned in the desired spatial relationship to the heart, with axis 26 extending generally normal to the surface of the heart surrounding the ostium OS of a pulmonary vein PV.

The physician may verify the proper disposition of ablation device 18 relative to the heart by injecting a fluid contrast medium through the continuous passageway defined by lumen 30 and tube bore 28 and out through port 29 on the distal or forward side of ablation device 18. Depending upon the pressure with which the contrast medium is injected, some portion of the contrast medium may pass into the pulmonary vein and other portions may remain within the left atrium. While the contrast medium is present, the subject is imaged using an imaging modality which will show the contrast medium as, for example, conventional x-ray or fluoroscopic imaging.

With the ablation apparatus properly positioned for ablation, the physician may actuate ultrasonic emitter 23, as by actuating an electrical energy source (not shown) connected to emitter 23 by conductors in catheter 12 (also not shown). Ultrasonic emitter 23 directs ultrasonic energy onto wall 24 between balloons 20 and 22, where the energy is reflected in a forward direction F and focused into the ring-like ablation region A. The focused ultrasonic energy heats and ablates the myocardial tissue in this region, thereby converting this tissue into scar tissue which is not capable of conducting electrical impulses.

The physician may detect electrical signals within the pulmonary vein or pulmonary vein ostium by inserting a sensor probe into the subject through the continuous passageway defined by lumen 30 and tube bore 28. Any one of the sensor probes described previously may be used. A method of using the sensor probes is described hereafter with reference to sensor probe shown in FIG. 2, however, the method is also applicable to the sensor probes shown in FIGS. 5 and 9 and any variations thereof. When using the sensor probe of FIG. 2 the physician manually straightens the hoop region and transition portion 84 as these are inserted through the proximal end of the catheter.

The probe body 78 has sufficient flexibility so that it can be advanced distally through the passageway. As the probe body 78 advances through catheter 12, the curvature of probe body 78 conforms to the existing curvature of catheter 12. As probe body 78 continues to advance, it reaches the condition shown in FIG. 2. The probe does not tend to buckle and jam as it is threaded through the passageway of the catheter. During threading, of course, the distal end portion is not in the hoop-shape shown, but instead is straight or slightly curved to match the curvature of the passageway in the catheter. As the physician continues to advance the sensor probe 72, the hoop region, distal end 76, and transition region pass distally out of port 26, the atraumatic tip leads the way. Since the atraumatic tip is the part of the hoop region that first contacts tissue, any potential tissue damage such as perforation of heart wall due to being poked by a sharp edge is prevented. Upon exiting port 26, the hoop region and transition region spring back to their unconstrained or deployed shape, as depicted in FIG. 4. This places hoop 82 concentric with axis 96 defined by main region 86 of probe body 78. However, because main region 86 is disposed within tube bore 28 of ablation device 18, main region 86 is coaxial with axis 26 of ablation device 18. Thus, hoop 82 tends to deploy in a plane perpendicular to axis 26 of the ablation device, with hoop 82 concentric with axis 26. As mentioned above, during placement of ablation device 18, the physician has already positioned this axis 26 in alignment with the pulmonary vein ostium and has positioned this axis 26 generally normal to the plane of the heart tissue encircling the ostium. Thus, hoop 82 tends to deploy in a location as shown in FIG. 1, with hoop 82 lodged within the pulmonary vein ostium, or (depending upon the diameter of the pulmonary vein) in the pulmonary vein itself, and with hoop 82 lying in the plane transverse to the axis of the pulmonary vein and the axis of the pulmonary vein ostium. All of this is accomplished without substantial manipulation by the physician to aim or locate hoop 82. Stated another way, ablation device 18 and catheter 12 act as an introducer structure which directs the distal portion of sensor probe 72 into alignment with the pulmonary vein ostium. Thus, placement of sensor probe 72 can be accomplished readily.

Although catheter 12 and ablation device 18 act to introduce and aim the hoop region of the sensor, the hoop region is not rigidly mounted to ablation device 18 or catheter 12, and hence, is not rigidly positioned by these devices. Transition region has some flexibility, so that hoop 82 can be displaced or tilted somewhat from perfect coaxial alignment with ablation device 18. This allows the hoop region to engage the tissues substantially around the pulmonary vein or ostium, even where these anatomical features are not perfectly aligned with the axis of ablation device 18. Also, hoop 82 has some flexibility, and accordingly can conform to these structures, even where the same are not perfectly circular.

With hoop 82 engaged with the tissues, electrodes 80 on hoop 82 will also be engaged with the tissues and hence will receive electrical signals propagating within the tissues. The physician can monitor these electrical signals using a conventional signal detection system 99 (FIG. 1) connected to a connector 88 and hence connected to electrodes 80 through conductors 92 (FIG. 3) of sensor probe 72. If these electrical signals indicate that abnormal conduction is continuing to occur, the physician can actuate the ablation device again. Sensing probe 72 need not be removed from the device during such further ablation. Alternatively, sensing probe 72 may be removed and other procedures, such as injection of additional contrast medium to confirm the desired disposition of ablation device 18, may be performed. In a further variant, sensor probe 72 may be introduced and placed as described above before actuation of ablation device 18, most typically after correct placement of ablation device 18 has been confirmed, as by use of the contrast medium technique discussed above.

In a further variant, ablation device 18 can be repositioned to a new position as partially depicted in broken lines at 18' in FIG. 1. Sensor probe 72 may be retracted into catheter 12 and ablation device 18, or may be entirely removed during the repositioning step. The same steps as discussed above may be repeated. The ability to retract or entirely remove sensor probe 72 facilitates repositioning. For example, contrast medium may be injected again to confirm the moved position of the apparatus. Also, because sensor probe 72 does not project from the apparatus during the repositioning step, it does not interfere with repositioning.

Figure 17:
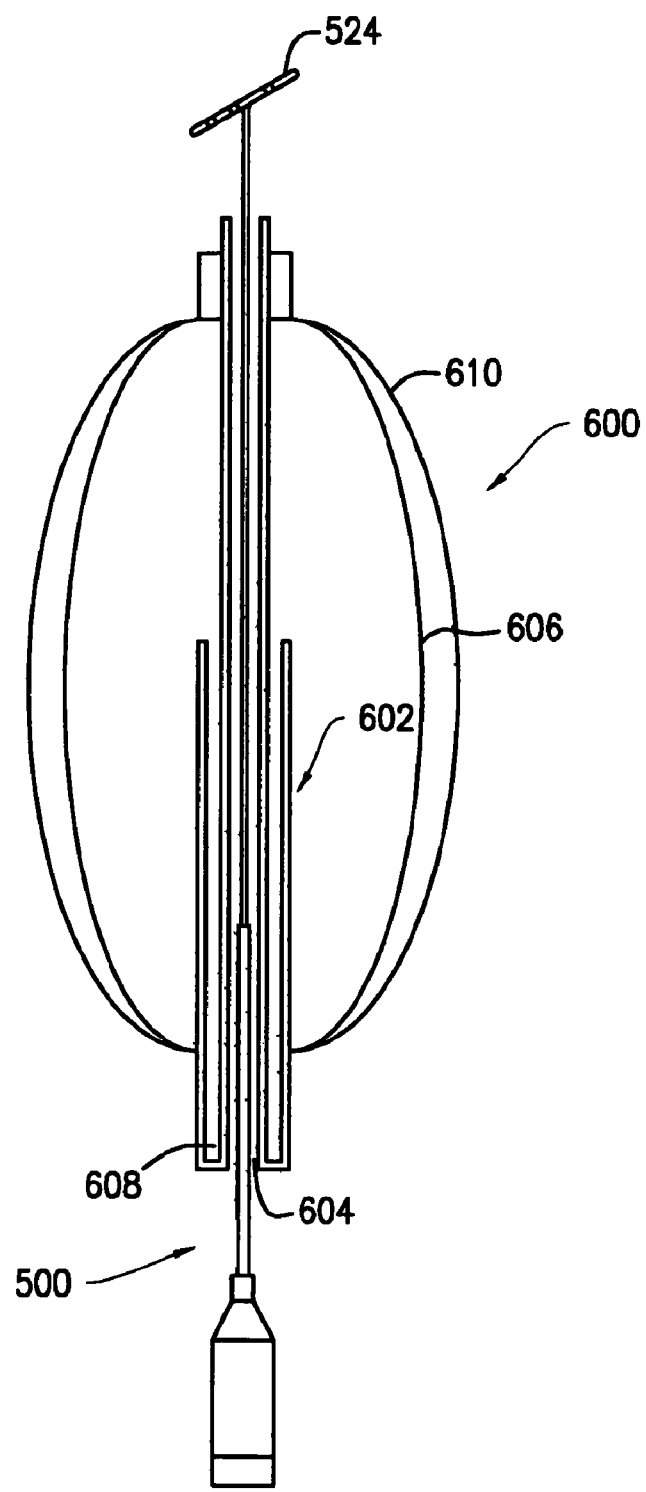
FIG. 17 is a schematic view of an ablation device using cryogenic energy with sensor probe of FIG. 13 inserted therein.

The various embodiments of sensor probes described above can be used with any ablation devices. For example, the sensor probes may be used with ablation devices that use cryogenic energy or laser energy or microwave energy or radiation energy or chemical ablation. To use the sensor probes described above, one only needs to provide a suitable lumen in the ablation device of choice. FIG. 17 shows, as an example, sensor probe 500 being used with an ablation device that used cryogenic energy to ablate the tissue. A cryogenic ablation device removes energy from the tissue to cool the tissue and thereby ablate the tissue. Cryogenic ablation device 600 includes a catheter 602 having a lumen 604 for insertion of a guide wire or a sensor probe 500. An inner balloon 606 is mounted on catheter 602. The distal and proximal ends of inner balloon 606 are attached to catheter 602 thereby enclosing a sealed volume between catheter 602 and balloon 606. An injection tube 608 with an open end located inside inner balloon 606 is formed in the catheter 602. A safety balloon 610 surrounds the inner balloon. Ablation device 600 may have steering that allows it to be moved around in the body to precisely place it inside the body cavity.

In use ablation device 600 is positioned within a chamber of the heart as, for example, within the left atrium LA of a subject to be treated. Typically, the ablation device 600 is advanced with balloons 606 and 610 in a deflated, collapsed condition. This operation may be performed by first advancing a guide wire (not shown) into the heart, and then advancing ablation device 600 over the guide wire. It is contemplated that ablation devices that do not have balloons may also be positioned in the heart chamber using a guide wire. Next, the balloon is deployed, sensor probe 500 is inserted in lumen 604 and loop 524 is deployed in the heart. Once ablation device 600 is in position, refrigerant is delivered through an injection tube 608 that is formed in catheter 602. The refrigerant provides the cryogenic energy to ablate the tissue that is in contact with the now inflated inner balloon 606 via safety balloon 610. After the tissue is exposed to the cryogenic energy for a predetermined period, the flow of refrigerant is stopped. Loop 524 is positioned in contact with the tissue where electrical conduction is to be measured and measurements are taken to determine if the tissue is conducting electrical charge. If the measurements indicate need for further ablation the balloon is repositioned to ablate tissue in appropriate location. Next, the electrical conduction is measured by appropriately positioning the loop 524 against the tissue. The process may be repeated as necessary without completely removing sensor probe 500 from lumen 604.

In an alternative method of use, sensor probe 500 monitors the effects of the ablation device 600 (or any other ablation device described herein) in real time, offering the physician important information. If an effect is seen (in say the first one minute) on the electrocardiograms, then the physician would choose to continue performing the ablation. If no effect is seen the physician may choose to abort the ablation prematurely and reposition the ablation device 600, thus saving time in an expensive to operate EP cath lab. This is particularly important with Cryo energy because the energy delivery (ablation) cycle times are long. They are typically on the order of four minutes. If a physician had to wait until the four minutes are up to measure effect this can add up to a really long procedure. It is not uncommon to have to deliver 10 to 20 energy cycles to achieve isolation. Therefore, the most important contribution the sensor probe 500 may offer the Cryo procedure is to shorten the procedure times.

As it will be clear to one skilled in art, sensor probe 500 may be inserted in the heart chamber via lumen 604 any time before or after ablation device 600 is positioned in the heart. The sensor probe 500 may also be used to anchor ablation device in the heart. Upon completion of the procedure, the sensor probe 500 may be withdrawn from the body.

For real time measurements, a pacing catheter is placed outside the pulmonary vein such as in the coronary sinus and the electrical signal induced by the pacing catheter in the heart tissue is monitored by loop 524 (of sensor probe 600) placed in the pulmonary vein to assess the state of conduction block surrounding the pulmonary vein. This can be done in real time as follows: As ablative energy is delivered from the ablation device 600 into the targeted myocardial tissue, loop 524 of sensor probe 600 continuously monitors electrocardiograms in the targeted PV. If the ablation device 600 is properly positioned and the ablative energy is directed where it is having the intended effect, the pulmonary vein potentials (PVPs) measured on loop 524 will demonstrate increased delay and ultimately achieve complete isolation (no PVPs measured). In this situation, observation of PVP delay and isolation occurs prior to the completion of the full ablation cycle time. In some cases, like in HIFU ablation procedures observation of PV isolation can occur in less than 10 seconds (out of a complete treatment cycle time of 40-90 seconds)

Conversely, if the ablation device 600 is delivering energy, the pacing catheter is pacing outside the Pv from within heart (such as in the coronary sinus), and loop 524 is monitoring electrocardiograms, and there is no observed effect to the electrocardiograms than this information suggests that the physician performing the procedure had positioned the ablation device 600 in a suboptimal position with respect to achieving Pv isolation. In this case, the physician can choose to abort the ablation cycle prematurely and reposition the ablation device 600. Over the course of a procedure, real time measurement of effect of ablation device 600 can reduce procedure times substantially. Particularly in light of the fact that it is not uncommon that twenty or more ablation cycles are required to achieve isolation of all PVs.

Numerous variations and combinations of the features discussed above can be utilized without departing from the present invention. The probe and method of probe deployment discussed above may be used for purposes other than sensing electrical signals in the context of an ablation process. For example, the probe can be used in a cardiac mapping operation, distinct from an ablation process. In a further variant, the functional elements of the probe (the sensing electrodes) may be used as ablation electrodes; or may be replaced by functional elements other than electrodes as, for example, discrete ultrasonic transducers or the like for an ablation process; or by sensors other than electrodes as, for example, chemical sensors. Further, although the present invention is particularly useful in performing procedures within the heart, it can be applied to performing procedures within other internal organs of a human or animal subject, or indeed, to performing procedures within a cavity of an inanimate subject.

The invention claimed is:

1. Apparatus for cardiac treatment comprising:
an elongated sensor probe having proximal and distal ends, the sensor probe including at least one electrode disposed adjacent the distal end of the sensor probe;
a ball formed at the tip of the distal end of the sensor probe; and
a floppy section attached to the ball, the floppy section having a wire core and a polymeric tube covering the wire core, the wire core having a reduced section attached to the ball, the polymeric tube being made from a soft material and having a reduced section and the wire core reduced section and the polymeric tube reduced section being in direct engagement such that there is no relative motion between them in the area near the ball.

2. The apparatus of claim 1, further comprising:
a catheter having proximal and distal ends; and
an ablation device mounted to the catheter at or adjacent the distal end thereof, the ablation device having a lumen therein and a port at a distal end of the lumen.

3. The apparatus of claim 2, wherein the sensor probe is adapted to be disposed in the lumen so that the sensor probe can be removably positioned in the lumen with the distal end of the sensor probe projecting out of the ablation device through the port.

4. The apparatus of claim 3, wherein the probe has a shaft portion having a circular cross-section, the diameter of the circular cross-section being about 35 mils.

5. The apparatus of claim 4, wherein the ablation device ablates the tissue by exposing it to ultrasound energy, cryogenic energy, chemical, laser beam, microwave, or radiation energy.

6. The apparatus of claim 5, wherein the electrodes are arranged in pairs such that a pair has two electrodes having a first space between them, and the pairs of electrodes have a second space between them.

7. The apparatus of claim 6, wherein the space between two electrodes forming the pair is greater than 0.50 mm.

8. The apparatus of claim 7, wherein the space between two adjacent pairs is greater than 1 mm.

9. The apparatus of claim 6, wherein the shaft portion comprises a hollow Nitinol shaft.

10. The apparatus of claim 9, wherein the wire core comprises Nitinol and is at least partially disposed within the hollow Nitinol shaft.

11. Apparatus for cardiac treatment comprising:
  an elongated sensor probe having proximal and distal ends, the sensor probe including at least one electrode disposed adjacent the distal end of the sensor probe;
  a ball formed at the tip of the distal end of the sensor probe; and
  a floppy section attached to the ball, the floppy section having a wire core and a polymeric tube covering the wire core, the wire core having a reduced section attached to the ball, the polymeric tube having a durometer in the range of 35 and 72 shore D and having a reduced section and the wire core reduced section and the polymeric tube reduced section being in direct engagement such that there is no relative motion between them in the area near the ball.

12. The apparatus of claim 11, wherein the wire core further comprises a tapered section, the tapered section tapering distally and adjoining the reduced section.

* * * * *